(12) United States Patent
Causevic et al.

(10) Patent No.: US 6,866,639 B2
(45) Date of Patent: Mar. 15, 2005

(54) HANDHELD LOW VOLTAGE TESTING DEVICE

(75) Inventors: Elvir Causevic, Ellisville, MO (US); Eldar Causevic, Ellisville, MO (US); Randall J. Krohn, Wildwood, MO (US)

(73) Assignee: Everest Biomedical Instruments, St. Louis, MO (US)

( * ) Notice: Subject to any disclaimer, the term of this patent is extended or adjusted under 35 U.S.C. 154(b) by 43 days.

(21) Appl. No.: 10/252,345

(22) Filed: Sep. 23, 2002

(65) Prior Publication Data

US 2004/0059250 A1 Mar. 25, 2004

(51) Int. Cl.$^7$ ............................. A61B 5/00; A61B 5/04
(52) U.S. Cl. ..................... 600/559; 600/544; 600/546; 600/300; 73/585
(58) Field of Search ................................ 600/300, 301, 600/509–523, 544–547, 554, 559; 73/585; 128/897, 901, 908, 920

(56) References Cited

U.S. PATENT DOCUMENTS

| | | |
|---|---|---|
| 3,396,673 A | 8/1968 | Livelsberger et al. |
| 5,197,332 A | 3/1993 | Shennib |
| 5,267,571 A | 12/1993 | Zurek et al. |
| 5,601,091 A | 2/1997 | Dolphin |
| 5,738,633 A | 4/1998 | Christiansen |
| 5,827,179 A | 10/1998 | Lichter et al. |
| 5,868,682 A | 2/1999 | Combs et al. |
| 5,916,174 A | 6/1999 | Dolphin |
| 6,159,147 A | 12/2000 | Lichter et al. |
| 6,231,521 B1 * | 5/2001 | Zoth et al. .................. 500/559 |
| 6,299,584 B1 * | 10/2001 | Iseberg ....................... 600/559 |
| 6,640,121 B1 * | 10/2003 | Telischi et al. ............. 600/379 |
| 2003/0073915 A1 * | 4/2003 | McLeod et al. ............ 600/509 |

FOREIGN PATENT DOCUMENTS

WO   0065983   11/2000

OTHER PUBLICATIONS

OAE—Frame Overlap Method for OAE Signal Detection/ Elvir and Eldar Causevic Oct. 1, 1998—1 page.
Kedly, Incorporated—AUDIOscreener—"Complete Solution to Universal Neonatal Hearing Screening"—1 page—no date.
Kedly, Incorporated—AUDIOall–Diagnostic—"Complete Solution to Comprehensive Hearing Diagnostics"—1 page—no date.
Kedly—AUDIOscreener (OAE) "Distortion Product Otoacoustic Emission Auditory Screening Device"—Operating Manual—Revision 6—Revision Date—Feb. 16, 2000—pp. 1–27.
SNAP™ Handheld EEG Monitor Product Specifications—Nicolet Biomedical, a division of VIASYS Healthcare—p. 1 of 1—May 2002.
Visor SNAP™ User Guide—Nicolet Biomedical SNAP—Nicolet VIASYS Healthcare—Jul. 2002—50 pages.
SNAP™ Changes Everything. "Put the power to measure EEG in the palm of your hand." —Transform Your PDA into an EEG Monitoring Tool –2 pages in color.

* cited by examiner

Primary Examiner—Charles Marmor
(74) Attorney, Agent, or Firm—Polster Lieder Woodruff & Lucchesi, L.C.

(57) ABSTRACT

A portable hand-held electrical testing device including a processor housed within an enclosure. The processor is configured to operate on commands by a user to process sub-microvolt electrical signals received through an input/output interface. The input/output interface includes a capacitive coupled amplifier with adjustable gain settings. Onboard memory linked to the processor stores processing data and instructions. A display device is mounted to said enclosure and is operatively connected to the processor to display processing results in real time.

22 Claims, 6 Drawing Sheets

HANDHELD LOW VOLTAGE TESTING DEVICE

CROSS-REFERENCE TO RELATED APPLICATIONS

None.

STATEMENT REGARDING FEDERALLY SPONSORED RESEARCH

Not Applicable.

BACKGROUND OF THE INVENTION

This invention relates to the field of low voltage electrical signal measurement devices and in particular, to the design of a hand-held sub-microvolt electrical signal measurement device. While the invention is described with particular emphasis to its use with auditory screening applications, those skilled in the art will recognize the wider applicability of the inventive principles such as vibration monitoring, gas monitoring, blood analysis, and alcohol intoximeters, such as disclosed hereinafter.

Test equipment capable of accurately measuring low voltage electrical signals in the sub-microvolt range has a wide range of applications from the monitoring of bioelectric signals in a human body, such as those found in the auditory system, to vibration monitoring and the measurement of electrical signals from chemical reactions such as found in alcohol intoximeters, more commonly referred to as breathalyzers. Low voltage electrical signals in the sub-microvolt range can be extremely difficult to detect, as often the signal noise levels and interference present can mask the desired signals. Handheld test equipment, in which numerous electrical circuits are packaged in close proximity, is particularly susceptible to such signal noise and interference. However, many of the applications in which the measurement of low-voltage electrical signals in the sub-microvolt range is required would benefit greatly from the use of portable, self-contained, hand-held test instruments.

For example, universal neonatal auditory screening programs have expanded greatly because of improved auditory measurement capability, improved rehabilitation strategies, increased awareness of the dramatic benefits of early intervention for hearing impaired babies, and changes in governmental policies. Current neonatal auditory screening approaches, however, do not account adequately for the many different types and degrees of auditory abnormalities that are encountered with present screening approaches. Because of this, individual screening tests based on a single measurement can be influenced negatively by interaction among various independent auditory abnormalities.

Current screening approaches have not considered adequately the entire screening program including: (i) physical characteristics of the measurement device i.e., portability, physical size and ease of use, (ii) operational characteristics of the device i.e., battery life, amount of record storage, required operating training, etc. and/or (iii) program logistics i.e., retesting mechanisms, referral mechanisms, record processing, patient tracking, report writing, and other practical aspects. These factors can interact negatively to increase the total cost of an auditory screening program, including the primary economic cost of screening and testing, the secondary economic cost of additional testing, and non-economic costs such as parental anxiety incurred when provided with incorrect information.

These costs, both actual and human, can be reduced by reducing the cost per test, reducing the false positive rate, and resolving false positive screening results at the bedside prior to hospital discharge. The cost per screening can be reduced with a dedicated device optimized for screening in any location and enhanced to allow effective operation by minimally trained personnel. The performance characteristic of the device of our invention includes reduced measurement time, the ability to operate and configure without an external computer, the ability to integrate and interpret all test results, the ability to store a large number of test results, long battery life, and bi-directional wireless transfer of data to and from external devices.

False positive results can be reduced in two ways. First, the initial screening test performance can be improved with enhanced signal processing, more efficient test parameters, and by combining different types of tests. Second, false positive rates also can be reduced by providing a mechanism for resolving an initial screening test failure at the bedside at the time of the initial screening. This capability is provided through the availability of an automated screening auditory brainstem response (ABR) test capability provided by the same device. Secondly, operational processes of a screening program can be improved through the use of several onboard computer based expert systems. These computer based expert systems provide improved automatic interpretation of single test results, automatic interpretation of multiple test results, and improved referral processes through the matching of local referral sources with various test outcomes, such as a referral to a specific type of follow-up, whether it be a pediatrician, audiologist, otolaryngologist, or a nurse. The device disclosed hereinafter integrates in a single, hand-held device, a single stimulus transducer, a single processor and a single software application for otoacoustic emission (OAE) and ABR testing.

An auditory abnormality is not a single, clearly defined entity with a single cause, a single referral source and a single intervention strategy. The peripheral auditory system has three separate divisions, the external ear, the middle ear, and the sensorineural portion consisting of the inner ear or cochlea, and the eight cranial nerves. Abnormalities can and do exist independently in all three divisions and these individual abnormalities require different intervention and treatment. Prior art physical and operational characteristics of devices and their influences on program logistics can interact negatively to increase the total cost of an auditory screening program. The primary economic cost is the cost of each screening test though this is not the only economic cost. A screening test failure is called a "refer" and usually is resolved with an expensive full diagnostic test scheduled several weeks after hospital discharge, resulting in significant economic cost. A substantial portion of these costs is unnecessary if the screening false positive rate is high. Non economic costs include parental anxiety for false positive screening results, unfavorable professional perception of program effectiveness for programs with high false positive rates and even inappropriate professional intervention because of misleading screening results.

The invention of multiple measurements into a single hand-held instrument allows for very important new functionality not available with existing neonatal auditory screening devices. This functionality includes (1) detection of common external and middle ear abnormalities; (2) the detection of less common sensorineural hearing loss associated with outer hair cell abnormalities, and (3) the detection of even less common sensorineural hearing loss associated with inner hair cell or auditory nerve abnormality.

Moreover, the device disclosed hereinafter has the potential to improve the accuracy and reliability of OAE measurements, to allow for optimal interpretation of both the OAE and ABR results, and to improve the referral process.

Attempts have been made in the past to provide the capabilities provided by the present invention. In particular, U.S. Pat. Nos. 5,601,091 ('091) and 5,916,174 ('174) disclose audio screening apparatus which purport to provide a hand-held portable screening device. However, the screening device disclosed in those patents is used in conjunction with a conventional computer, and requires a docking station for full application use. In no way does the disclosure of either patent provide a hand-held device that can be used independently of any other computer. That is to say, the invention disclosed hereinafter provides a device of significantly reduced size i.e., hand-held, which is capable of providing OAE and ABR testing. It can be operated in a stand-alone mode, independently of any other computer connection, if desired. The device includes a patient database, with names, and full graphic display capability. The device also preferably is provided with a wireless infrared and an RS 232 connection port to provide output directly to printers or to a larger database where such is required. The '174 and '091 patents also operate on a linear averaging method to remove background noise. While such a method works well for its intended purposes, use of a linear averaging method is time consuming.

Accordingly, there is a need for portable, hand-held test equipment capable of accurately measuring low voltage electrical signals in the sub-microvolt range, and which is capable of providing improved signal reliability in a reduced time frame using an on-board processor to access and store information in an associated memory storage device.

BRIEF SUMMARY OF THE INVENTION

Briefly stated, an effective sub-microvolt electric testing device is provided. In the preferred embodiment, the device includes a portable hand-held enclosure containing a digital signal processor. The processor has a memory and a computer program associated with it for control of CODEC components capable of generating sub-microvolt electrical output signals on four discrete output channels and for receiving sub-microvolt electrical input signals on four discrete input channels. A display device is mounted to the enclosure, and displays test information, test setup procedures, and test results including the graphing of test results. The enclosure includes a connection point for one or more probes, the connection point being operatively connected to the digital signal processor. The device also includes an onboard power supply, making the device completely self contained.

In one embodiment of the present invention, an effective auditory screening device is provided. The integration of an OAE screening device and ABR screening device into a single, hand-held instrument enables a user to detect less common sensorineural hearing loss associated with outer hair cell abnormalities and the detection of less common sensor hearing loss associated with inner hair cell abnormalities. In the preferred embodiment, the device includes a portable hand-held enclosure containing a digital signal processor. The processor has a computer program associated with it, capable of conducting both otoacoustic emission test procedures and auditory brainstem response test procedures for a test subject. A display device is mounted to the enclosure, and displays patient information, auditory screening setup procedures, and auditory screening test results, including graphical analysis. The enclosure includes a connection point for a probe, the connection point being operatively connected to the signal processor. The device also includes an onboard power supply, making the device completely self contained.

The foregoing and other objects, features, and advantages of the invention as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings.

DESCRIPTION OF THE PREFERRED EMBODIMENT

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

Figure 1:
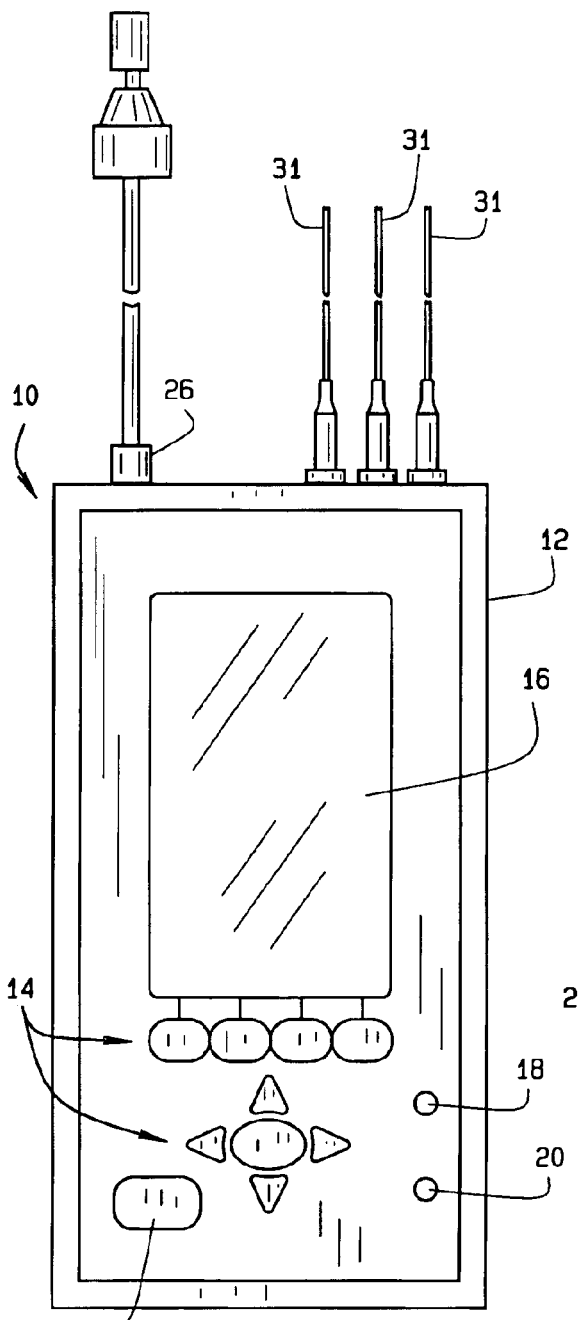
FIG. 1 is a top plan view of one illustrative embodiment of an electrical testing device of the present invention.
Figure 2:
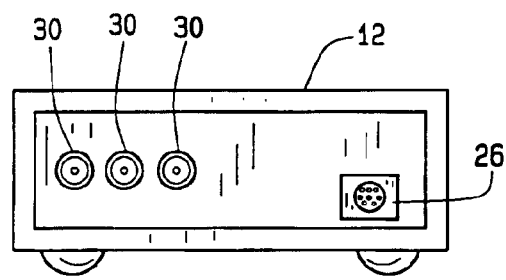
FIG. 2 is a view in end elevation of the electrical testing device.
Figure 3:
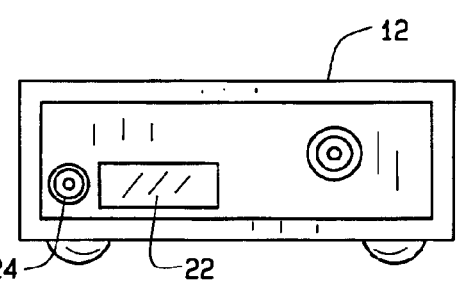
FIG. 3 is a view in end elevation of the electrical testing device end opposite to that shown in FIG. 2.

Referring now to FIG. 1 through FIG. 3, reference numeral 10 illustrates one embodiment of the hand-held sub-microvolt electrical signal measurement device of the present invention. The measurement device 10 includes an enclosure 12, which in the preferred embodiment, and for purposes of illustration and not for limitation, measures 7¼" long by 3¾" wide by 1½" deep. It is important to note that the device 10 can be carried by the user without compromise, and truly represents a portable hand-held device having full functionality as described below. The device 10 includes a keyboard 14 and an LCD display 16. One or more LED indicators are optionally included, such as an LED pass/refer indicator 18, and an LED AC charging indicator 20. Again, by way of illustration and not by limitation, it should be noted that the LCD display 16 measures, in the preferred embodiment, approximately, 2" by 3⅜". The measurement is not necessarily important, except to show that the LCD display 16 is fully functional for a user, and the device 10 can operate independently of any other computer system.

In the embodiment illustrated, the enclosure 12 also houses an infrared port 22, and a compatible RS-232 port 24, a probe connection 26 suitable for use with an input probe 28, such as an ear probe, and an interface 30 for a plurality of output electrodes 31. Probe 28 is convention and is not described in detail. Suitable probes, such as ear probes, are commercially available from Etymotic Research, Pat. Nos. ER-10C, ER-10D, and GSI 2002-3250, for example.

Figure 4:
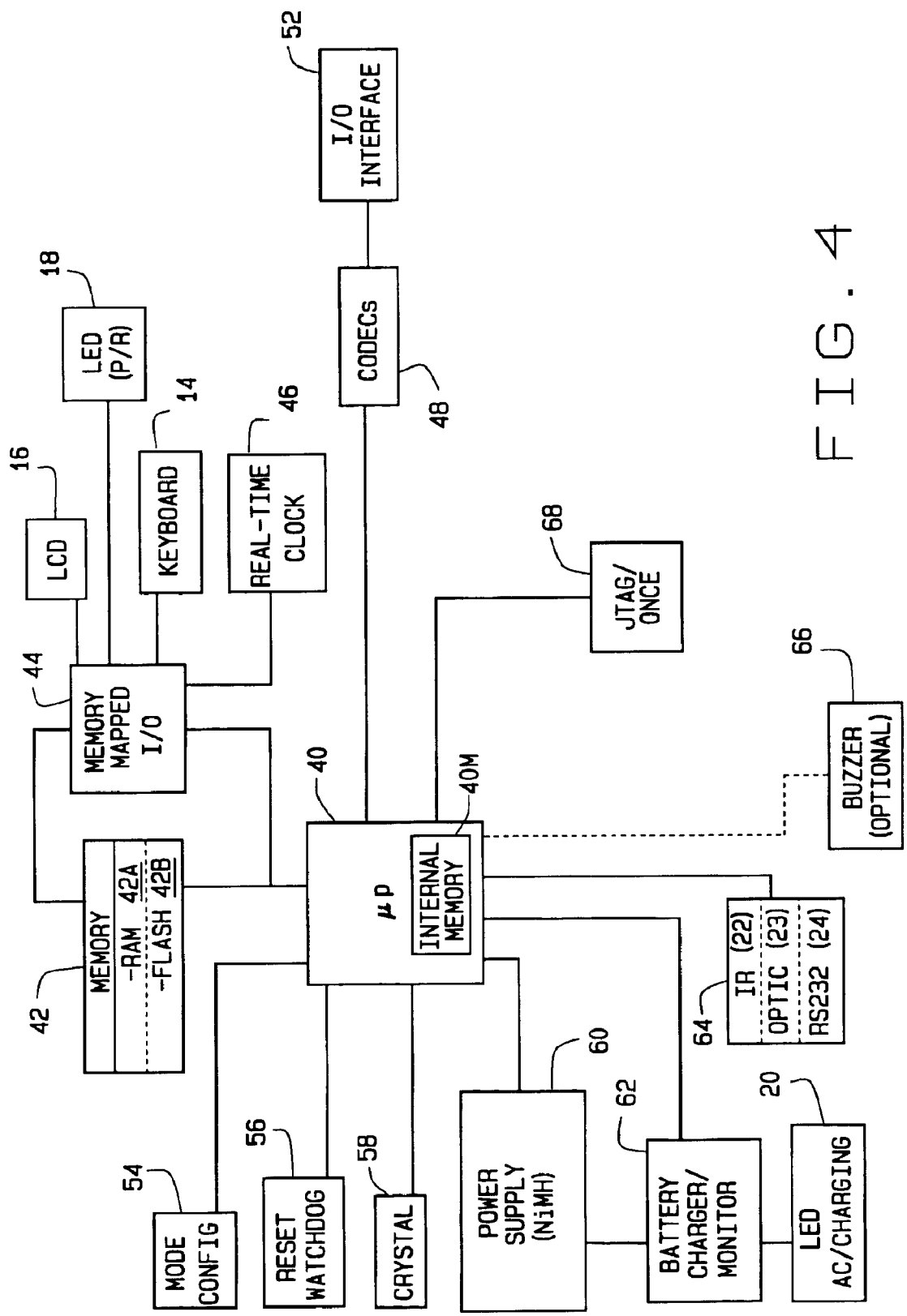
FIG. 4 is a block diagrammatic view of an electrical testing device shown in FIG. 1.

Referring now to FIG. 4, a block diagram view of the hand-held sub-microvolt electrical signal measurement device 10 is shown and described. Preferably, the system shown in FIG. 4 is manufactured on a single printed circuit board, with mixed signal design for both analog and digital operation. The device 10 preferably is low powered, and generally operates at 3.3 volts, except for the LCD display 16 and some low power portions of the analog circuitry employed with the device 10. To reduce undesired signal interference, it has been found that it is preferable that all analog and digital circuit components share a common electrical ground point within the device 10.

A suitable micro-processor 40 is the control for the device 10. In the preferred embodiment illustrated, the processor 40 is a Motorola model No. 56303 digital signal processor, however, those of ordinary skill in the art will recognize that any suitable micro-processor or micro-controller having sufficient computational power and speed may be utilized. All signal processing functions described hereinafter are performed by the processor 40, as well as the control of all input and output functions of the device 10. In addition, graphic functions, user interface functions, data storage functions, and other device functionality are controlled by the processor 40.

In conventional design logic, the digital signal processor 40 is used for signal processing, and a separate micro-controller is used for device control. In device 10, the digital signal processor 40 performs the functions of the separate micro-controller in addition to signal processing, eliminating the requirement of a separate micro-controller, resulting in substantial savings in circuit board space, manufacturing cost and operational power consumption.

To reduce undesired signal interference during the data-acquisition phase of operations, the processor 40 in device 10 is either shut-down or switched to a "sleep" mode during data collection operations, which can be carried out independently of the processor 40. Further reduction in external signal noise is achieved by the execution of software in data and program memory 40M internal to processor 40, thereby eliminating external bus access signal noise.

A memory subsystem 42 is operatively connected to the processor 40. The memory subsystem 42 includes a random access memory (RAM) 42A for storing intermediate results and holding temporary variables, and a flash memory 42B for storing non-volatile, electrically programmable variables, test result data and system configuration information. In the embodiment illustrated, the flash memory 42B is substantially oversized, enabling the device 10 to accommodate several hundred data records, as well as multiple configurations files.

A memory mapped input/output device 44 is operatively connected to the memory subsystem 42 and to the digital signal processor 40. The memory mapped input/output 44 in turn is operatively connected to the LCD display 16, the keyboard 14, an output LED indicator 18 and a real time clock 46.

The LCD display 16 provides the user with a display array preferably having a minimum size of 128×256 pixels. A display array of this size is sufficient to present full wave-forms of signal tests conducted by the device 10. The device 10 enables the LCD 16 to present signal information to a user graphically in real time on the device 10 itself, complemented with textual and numeric information about the quality of the data, signal amplitudes, signal frequency, noise floors and other related signal information.

The keyboard 14 preferably is a membrane switch keyboard, which incorporates only the minimum keys necessary for operation of the device 10. All keys are programmable, except for an On/Off key 15.

The real-time clock 46 is operatively connected to the processor 40 through the memory mapped input/output device 44. The real-time clock 46 enables the processor 40 to provide a time stamp for each data collection or test performed.

The output LED 18 is used to convey test results to non-trained users to avoid confusion or misinterpretation of the LCD graphics display 16. For example, the processor 40 may be programmed to illuminate the output LED 18 in response to a predetermined input criteria, such as an input signal strength exceeding a predetermined minimum value. The output LED 18 further allows the use of the device 10 in low light areas, where the LCD display 16 may be difficult to read or interpret.

The plurality of analog to digital/digital to analog coder/decoders 48 (codecs 48) are operatively connected to the signal processor 40 along a dedicated serial link. As will be appreciated by those skilled in the art, the codecs 48 are special integrated circuit chips that perform analog to digital and digital to analog conversion. The codecs 48 in turn are operatively associated with a one or more input/output devices interfaces 52, which provide the functionality of the device 10 under control of the processor 40. Preferably, the digital signals generated and received by codecs 48 have 20-bit resolution for both analog to digital and digital to analog conversions.

Figure 5:
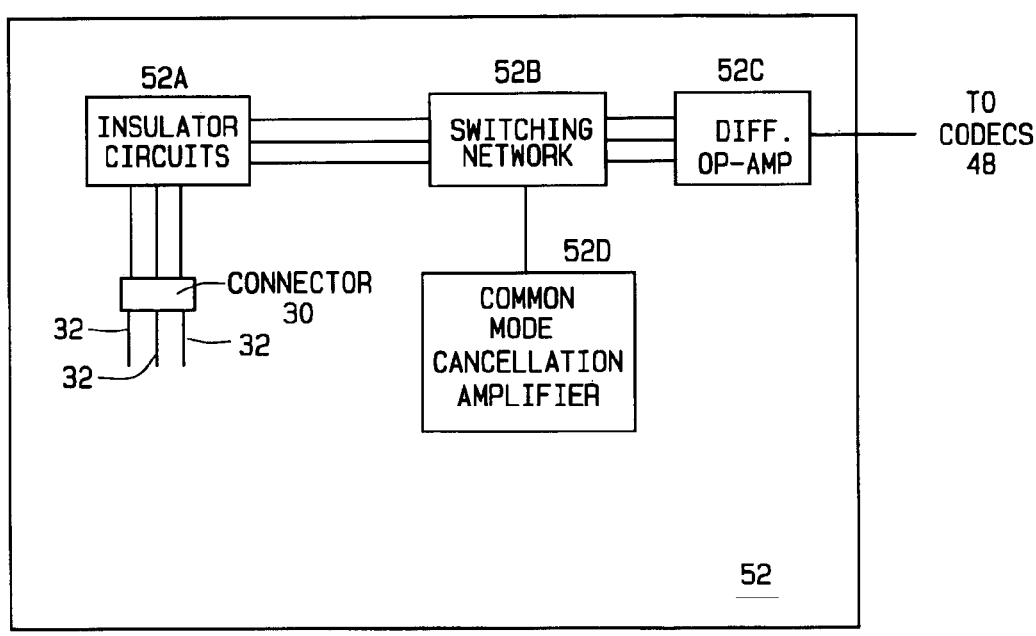
FIG. 5 is a block diagrammatic view of a second set of generic electrical input and output channels shown in FIG. 4.

In one embodiment of the present invention 10, input/output interface 52 includes four input channels and four output channels adapted for sub-microvolt electrical signals. As shown in FIG. 5, the input/output interface 52 consists of a plurality of analog signal processing chips, not shown individually, which filter and amplify the signals received from a number of discrete input channels 32. Specifically, signals received from each input channel 32 are routed through an electrical insulator circuit 52A, consisting of a plurality of metal oxide varistors, resistors, and capacitors, which function as surge arrestors to isolate the input channels 32 from any dangerous electrical currents or voltages. The insulator circuit 52A functions to replace conventional insulator circuits which utilize optical signal pathways, thereby eliminating the associated signal noise resulting from the conversion between electrical signals and optical signals.

Signals from the input channels 32 are then routed through a switching network 52B, wherein an individual signal is automatically selected and passed to a capacitive coupled differential operational amplifier 52C having high gain. A common mode cancellation amplifier 52D is included in the input/output interface 52 to further reduce signal noise levels. The resulting amplified signal is then routed to the codecs 48. In addition to selecting an individual signal from the input channels 32, the switching network 52B permits a variety of signal measurements on the input channels 32 to be carried out using the same differential operational amplifier 52C, by altering the amplifier gain setting.

Returning to FIG. 4, a mode configuration system 54, a reset watchdog system 56, a clock crystal 58, a power supply 60, preferably a nickel-metal hydride battery, and a battery charger 62 all are also positioned within the enclosure 12 and operatively connected to the processor 40. While each of these blocks is required for operation of the device 10, they are standard in nature and are not described in detail.

The processor 40 has an input-output channel 64, which preferably includes an infrared connection 22, a fiber-optic connection 23 and an isolated RS-232 interface 24. The device 10 can communicate with any infrared compatible or RS-232 compatible personal computer, printer, or other digital device (not shown) for data transmission. Data transmission may include test subject information, configuration data for the signal processor 40, or software program updates for storage in the memory subsystem 42.

A audio output 66 in the form of a buzzer also is provided. The audio output 66 provides an audio feedback to the user for keyboard actions and an audio indication for error conditions.

A serial port 68 also is operatively connected to the processor 40. The serial port 68 is utilized to provide direct programming of the processor 40 from a personal computer, for example, and is intended for use only for initial software download and major software program upgrades of the processor 40.

Figure 6:
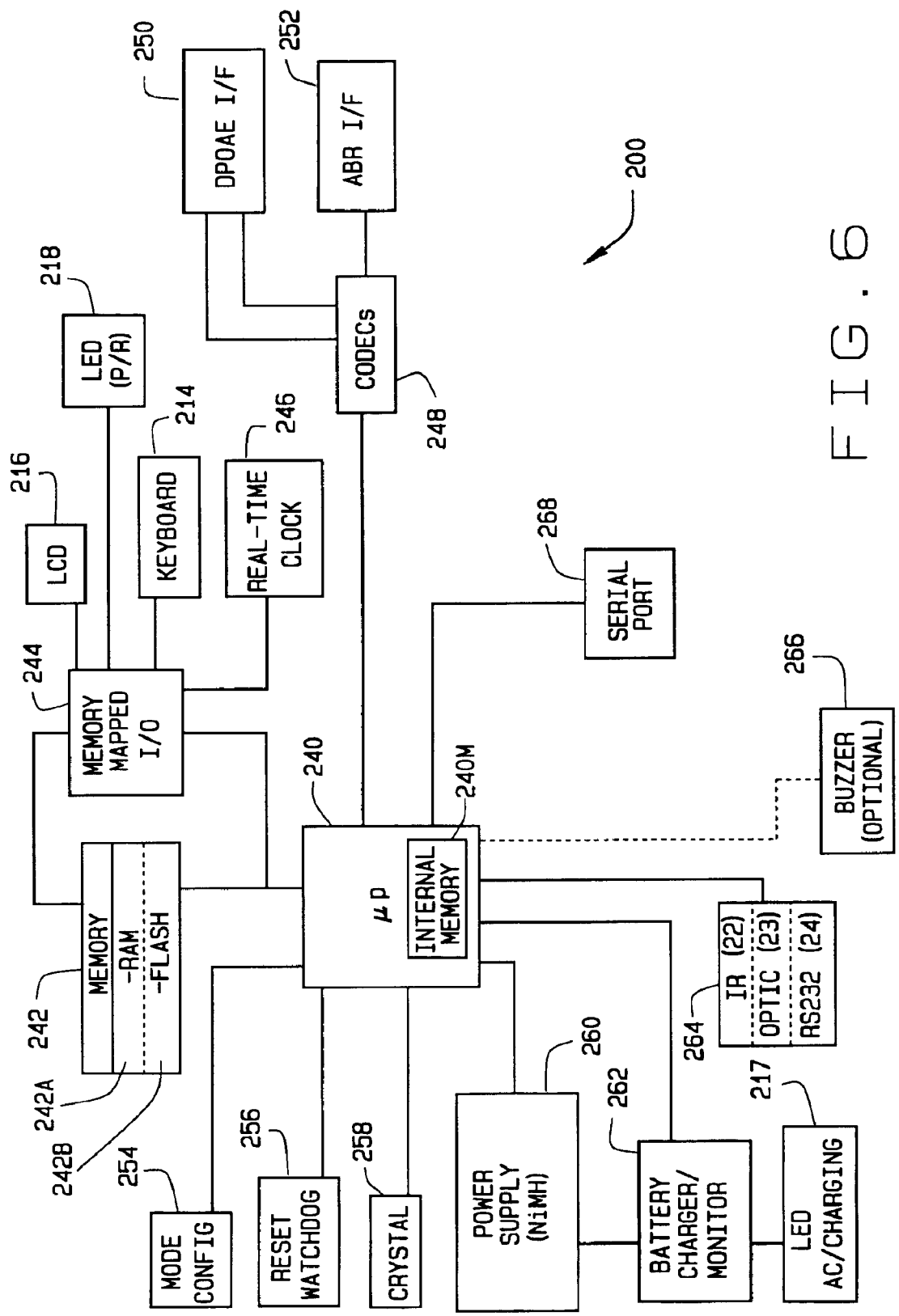
FIG. 6 is a block diagrammatic view of an auditory screening embodiment of the electrical testing device shown in FIG. 1.
Figure 7:
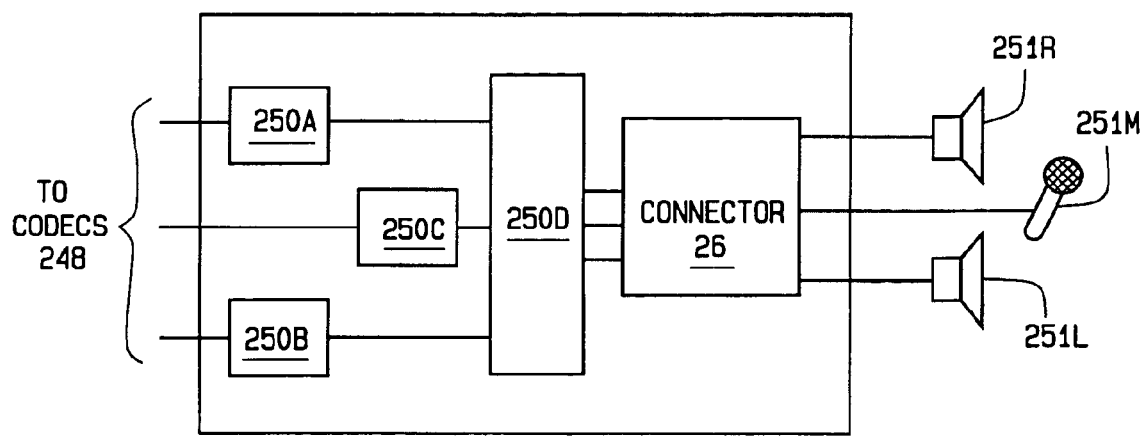
FIG. 7 is a block diagrammatic view of the DPOAE interface in FIG. 6.

Referring now to FIG. 6, a block diagram view of one embodiment of the device 10, configured for use as an auditory screening device 200, is shown and described. The device 200 contains OAE and ABR simulator capabilities in a single, hand-held package. Preferably, the system shown in FIG. 6 is manufactured on a single printed circuit board, with mixed signal design for both analog and digital operation. The device 200 preferably is low powered, and generally operates at 3.3 volts, except for the LCD display 216 and some low power portions of the analog circuitry employed with the device 200. To reduce undesired signal interference, it has been found that it is preferable that all analog and digital circuit components share a common electrical ground point within the device 200.

A digital signal processor 240 is the control for the device 200. In the preferred embodiment illustrated, the processor 240 is a Motorola model No. 56303 DSP. All signal processing functions described hereinafter are performed by the processor 240, as well as the control of all input and output functions of the device 200. In addition, the graphic functions, user interface, patient data storage functions and other device functionality are controlled by the processor 240. In conventional design logic, the digital signal processor 240 is used for signal processing, and a separate micro controller is used for device control. In device 200, the digital signal processor 240 performs the functions of the separate micro controller in addition to signal processing, eliminating the requirement of a separate microprocessor, resulting in substantial savings in circuit board space, manufacturing cost and operational power consumption. To reduce undesired signal interference during the data-acquisition phase of operations, the processor 240 in device 200 is either shut-down or switched to a "sleep" mode during data collection operations, which can be carried out independently of the processor 240. Further reduction in external signal noise is achieved by the execution of software in data and program memory 240M internal to processor 240, thereby eliminating external bus access signal noise.

A memory subsystem 242 is operatively connected to the processor 240. The memory subsystem 242 includes a random access memory (RAM) 242A for storing intermediate results and holding temporary variables, and a flash memory 242B for storing non-volatile, electrically programmable variables, patient data, and configuration information. In the embodiment illustrated, the flash memory 242B is substantially oversized, enabling the device 200 to accommodate several hundred full patient records, as well as multiple configurations files.

A memory mapped input/output device 244 is operatively connected to the memory subsystem 242 and to the digital signal processor 240. The memory mapped input/output 244 in turn is operatively connected to the LCD display 216, the keyboard 214, the pass/referral LED indicator 218 and a real time clock 246.

The LCD display 216 provides the user with a display array preferably having a minimum size of 128×256 pixels. A display array of this size is sufficient to present full waveforms of audiometric tests conducted by the device 200. The device 200 enables the LCD 216 to present signal information to a user graphically in real time on the device 200 itself, complemented with textual and numeric information about the quality of the data, signal amplitudes, signal frequency, noise floors and other related signal information.

The keyboard 214 preferably is a membrane switch keyboard, which incorporates only the minimum keys necessary for operation of the device 200. All keys are programmable, except for an On/Off key (not shown).

The real-time clock 246 is operatively connected to the processor 240 through the memory mapped input/output device 244. The real-time clock 246 enables the processor 240 to provide a time stamp for each patient and test performed, as well as providing time signals for internal operation of the device 200.

An LED AC charging indicator 217 provides a visual indication of battery charging status, while the LED pass/refer diode 218 is used to convey test results to non-trained users, namely a nurse as opposed to an audiologist or otolaryngologist. Use of the LED 218 avoids confusion or misinterpretation of the LCD graphics display 216, and allows use of the device 200 in low light areas, where the LCD display 216 may be difficult to interpret.

The plurality of analog to digital/digital to analog coder/decoders 248 (codecs 248) are operatively connected to the signal processor 240 along a dedicated serial link. As will be appreciated by those skilled in the art, the codecs 248 are special integrated circuit chips that perform analog to digital and digital to analog conversion. The codecs 248 in turn are operatively associated with a plurality of input/output devices, which provide the functionality of the device 200 under control of the processor 240.

An otoacoustic emission interface 250 (DPOAE I/F) is operatively connected to the signal processor 240 through the associated codecs 248. The otoacoustic emission interface 250 preferably is a low noise, differential analog circuit with high common mode noise rejection. As shown in FIG.

7, the otoacoustic emission interface 250 is intended to drive two sound transducers 251R, 251L through a pair of differential operational amplifiers 250A, 250B to produce a variety of signals, from pure tones at various frequencies to chirps, clicks, sine waveforms, etc. The otoacoustic emission interface 250 can present tones at standard sound pressure levels. The device employed with the otoacoustic emission interface 250 includes a microphone 251M, also inserted in the ear canal, which collects signals coming back from the ear, and provides sufficient linear amplification through a dual-stage amplifier 250C to present the signals to the codecs 248. The transducers and microphone interface circuits include a plurality of electrostatic discharge diodes and induction coils to provide electrical shock protection 250D. In various embodiments of this invention, the otoacoustic emission interface 250 also can be used for otoreflectance measurements for assessing some middle ear conditions.

Figure 8:
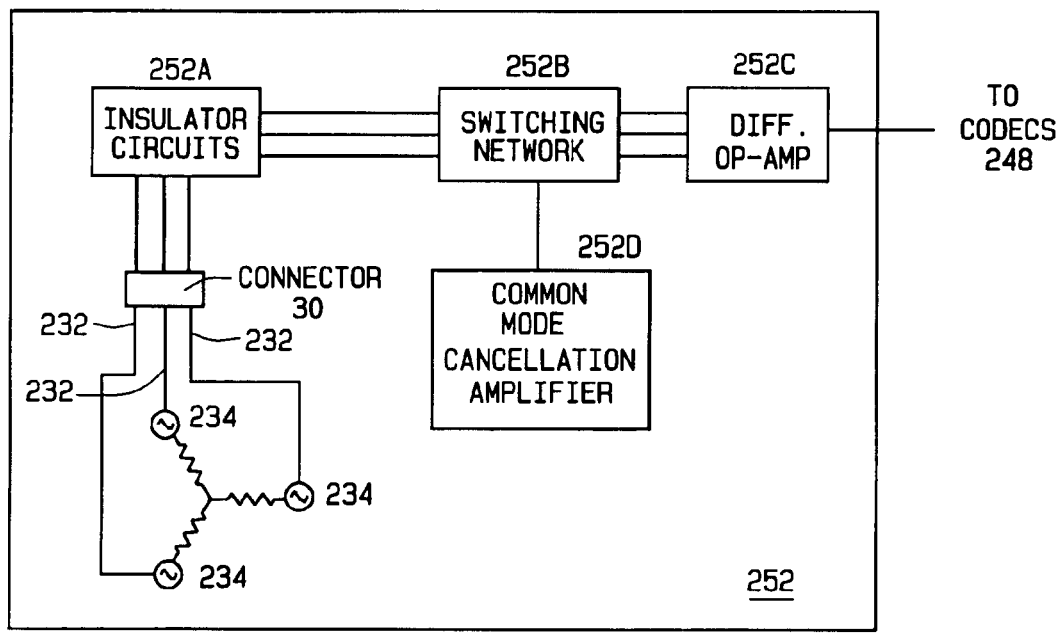
FIG. 8 is a block diagrammatic view of the ABR interface in FIG. 6.

The ABR interface 252, shown in FIG. 8, consists of a plurality of analog signal processing chips, not shown individually, which filter and amplify the signals received from the scalp of a subject via electrode wires 232. Specifically, signals received from each of the individual electrodes 234 are routed through an electrical insulator circuit 252A, consisting of a plurality of metal oxide varistors, resistors, and capacitors, which functions to isolate the electrodes 234 from any dangerous electrical currents or voltages. The insulator circuit 252A functions to replace conventional insulator circuits which utilize optical signal pathways, thereby eliminating the associated signal noise resulting from the conversion between electrical signals and optical signals. Signals from the electrodes 234 are then routed through a switching network 252B, wherein an individual signal is automatically selected and passed to a differential operational amplifier 252C. A common mode cancellation amplifier 252D is included in the ABR interface 252 to further reduce signal noise levels. The resulting amplified signal is then routed to the codecs 248.

In this mode of operation, the ear is presented with a repeated acoustic stimuli that cause neurons to fire beginning with the eighth cranial nerve and sequentially through neurons in the auditory pathways in the central nervous system from the brainstem to the cortex. Through the mechanism of volume conduction, the electrical potentials generated from these neuronal firings can be detected by the electrodes 234 on the surface of the skin.

An additional function of the ABR interface 252 is to provide automated impedance check of the placement of electrodes 234. Once the electrodes 234 are in place, a small current is injected through the electrodes 234 into the scalp of the subject, and the impedance between electrodes 234 is measured. In addition to selecting an individual signal from the electrodes 234, the switching network 252B permits impedance measurements of the electrodes 234 to be carried out using the same differential operational amplifier 252C, by altering the amplifier gain setting. Impedance can be varied by placement of the electrodes. Once the impedance is within the predetermined range for operation, ABR signal connection can begin. It is important to note that impedance checking can be accomplished without unplugging the electrodes. That is to say, checking is automatic.

Returning to FIG. 6, a mode configuration system 254, a reset watchdog system 256, a clock crystal 258, a power supply 260, preferably a nickel-metal hydride battery, and a battery charger 262 all are operatively connected to the processor 240. While each of these blocks is required for operation of the device 200, they are standard in nature and are not described in detail.

The processor 240 has an input-output channel 264, which preferably includes infrared connection 22, fiberoptic connection 23 and isolated RS-232 interface 24. The device 200 can communicate with any infrared compatible or RS-232 compatible personal computer, printer, or other digital device (not shown) for data transmission. Data transmission may include patient information, configuration data for the signal processor 240, or software program updates for storage in the memory subsystem 242.

A audio output 266 in the form of a buzzer may be provided. The audio output 266 provides an audio feedback to the user for keyboard actions and an audio indication for error conditions.

A serial port 268 also is operatively connected to the processor 240. The serial port 268 is utilized to provide direct programming of the processor 240 from a personal computer, for example, and is intended for use only for initial software download and major software program upgrades of the processor 240.

As an auditory screening device 200, the present invention utilizes a auditory phenomena known as a distortion product otoacoustic emission (DPOAE). A DPOAE is a tone generated by a normal ear in response to the application of two external tones. When two tones, $f^1$ and $f^2$ are applied to an ear, the normal non-linear outer hair cells generate a third tone $f^{dp}$, which is called a distortion product. The distortion product $f^{dp}$ then propagates from the outer hair cells back to the ear canal where it is emitted. The level of the DPOAE can be used as a measure of outer hair cell function. If the outer hair cell system is absent or otherwise not functioning properly, the non-linearity will be absent or reduced and the $f^{dp}$ will either not be generated or generated at a lower than expected level.

The measured DPOAE is highly dependent upon the specific tones that invoke it. The frequencies of $f^1$ and $f^2$, and their respective levels in the ear canal, L1 and L2 must be controlled precisely. Under known signal conditions, the largest distortion product $f^{dp}$ is generated at a very specific frequency ($f^{dp}=2f^1-f^2$), and level $L^{dp}$. Comparison of the level of $L^{dp}$ with known values from individuals with normal outer hair cell systems forms the basis of the decision of whether the patient either passed the screening, illuminating the pass/refer LED 218, or requires a referral for a more complete diagnostic testing.

Signals other than pure tones can be presented to the ear, which will also evoke an auditory response from the ear, such as clicks, chirps, etc. The DPOAE response is used with the auditory screening device 200 as an example of one such input. Other auditory stimuli generating an auditory response would be processed by the auditory screening device 200 the same way as the DPOAE.

Figure 9:
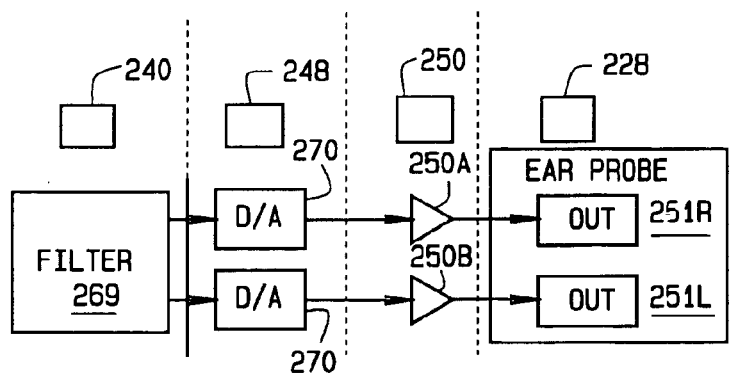
FIG. 9 is a block diagrammatic view of the signal output phase of the OAE testing employed with the device of FIG. 6.

As shown in FIG. 9, during operation, the processor 240 sends a filtered output signal from a filter 269 through the digital to analog converter portions 270 of the codecs 248. The output signals are then routed through amplifier components 250A and 250B in the DPOAE interface 250 and transmitted to the output components 251R and 251L of the ear probe 228 utilized in conjunction with the device 200.

Figure 10:
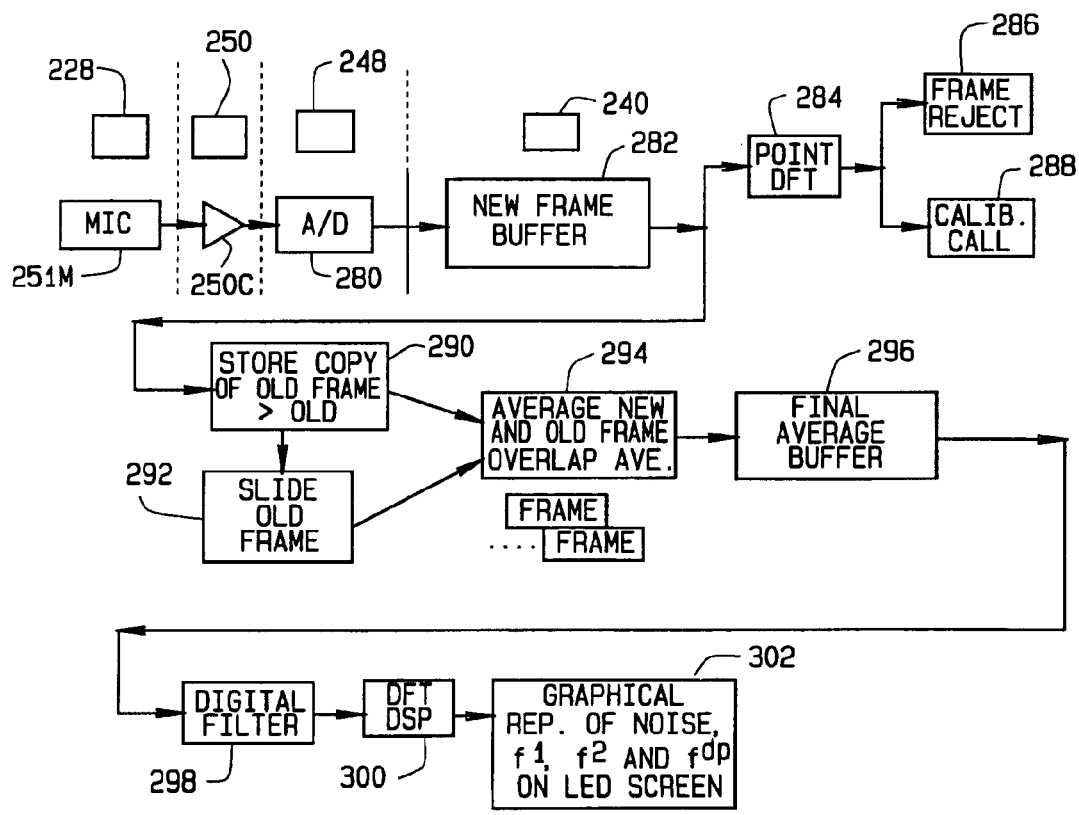
FIG. 10 is a block diagrammatic view of the signal input phase of the OAE testing employed with the device of FIG. 6.

As shown in FIG. 10, the ear probe 228 includes a microphone 251M which returns signals through a third amplifier 250C in the DPOAE interface 250. The amplified analog signal is routed through an analog-to-digital converter 280 in the codecs 248, and conveyed to the processor 240.

In the processor 240, the incoming analog signal is sampled using a frame buffer 282. The size of each new frame in the frame buffer 282 is calculated to be an integer number of samples of the two primary tones at frequencies $f^1$ and $f^2$, and also, an integer number of samples of the otoacoustic tone produced by the ear at $f^{dp}$. This is a critical step to assure quality of subsequent signaling processing, by avoiding windowing techniques, which can introduce substantial artifacts. Tables of numbers for each standard frequency employed in the device 200 and for other frequencies in use or intended use in the device 200 are available, and are programmed into the algorithm once the user selects the test frequencies. Should a combination of frequencies be required for which no common integer number can be found to fit in a practical size frame, the frame size is adjusted to $f^{dp}$ and the frame is windowed prior to Fourier Transformation, but this method is used only in extreme cases since in normal operation, the required frequencies are available.

The data from a single frame is passed to a point Discrete Fourier Transform (DFT) block 284 which calculates the signal's magnitude and phase content, but only at frequencies of interest, including $f^1$, $f^2$, and $f^{dp}$ to determine a noise floor. Windowing is induced prior to processing the DFT to reduce edge effects, although windowing induces energy at other bands. The block 284 is used only for temporary calculations, and the windowed data is not reused again. The output of block 284 is the magnitude and phase of primary signals at $f^1$ and $f^2$ and the noise floor figure of time at $f^{dp}$. The output of block 284 forms an input to frame rejection block 286 and to an on-line calibration calculation block 288.

With the information on the magnitudes at various frequencies, a noise calculation algorithm is employed at and/or around $f^{dp}$ to determine the noise floor. The magnitude of the noise floor and frequency content are used against a set of predetermined conditions, i.e. a comparison against an empirically derived table contained in the processor 240, to determine the outcome of the frame. That outcome has three distinct possibilities. First, if the noise magnitude and frame content exceed a multi-threshold condition at measured frequency bands, the new frame is rejected. Second, if the noise magnitudes fall between a set of reject thresholds and a set of accept thresholds, the data in the frame is disregarded, but the noise information is kept to update the noise level average. Third, if the noise magnitudes are below the accept thresholds, the frame is kept and passed on for further processing and the noise magnitudes are averaged together with the noise average of the previous frame. This information is used to update thresholds, such that the system adapts to environmental conditions.

When the information about magnitudes of primary tones at $f^1$ and $f^2$, and the noise floor information at and/or around $f^{dp}$, an online calibration of the level of magnitudes takes place. Several actions occur in the calibration block 288. First, if the noise floor is large when no primary tones are present, the frequency of the primaries is adjusted within predetermined limits. A new $f^{dp}$ is calculated, and the noise content of frequency bins at and around $f^{dp}$ is checked again. This process is repeated until a stable, low noise floor is established. No primary tones are played through the speaker through this process. Once the primaries are presented, they are stepped up to the full output amplitude, as programmed by the user and calibrated in the ear by increasing the output of the codecs 248. No data collection from the ear has taken place yet. At this time, if the level is not reached in a user predetermined time, and at the rate of increase of the primaries, the test is aborted due to lack of fit or the low quality of fit of the probe in the ear canal.

Once a proper fit of the probe in the ear canal is achieved, and testing begins, data collection takes place. During the entire process of data collection, the levels of tones at $f^1$ and $f^2$ are checked to ensure that they remain within predetermined limits throughout the test. If they exceed those limits, the output is adjusted up or down to compensate until a maximum compensation limit is reached, at which time, the test is aborted and the user is notified. Also, the magnitude at and/or around $f^{dp}$ is continuously monitored to assure low noise floor, and if necessary, the frequency of the primary tones are adjusted on-line within predetermined limits to avoid the high external noise region. The change in frequencies of the primaries is minimal, and within the specified tolerances of the device 200, and have been shown not to affect the magnitude of the tone within the ear at $f^{dp}$.

The block 290 is a store/copy buffer. As a frame of signal data is collected in new frame buffer 282, a copy of it is saved by the store/copy buffer 290 for processing of the subsequent frames. The store/copy buffer 290 receives frame data from new frame buffer 282 and has a variable depth, depending the number of frames averaged together. Buffer 290 provides an output to a slide buffer block 292 and an average buffer 294. The slide buffer 292 operates with the stored previous frames, which are slid by a predetermined amount and the empty spaces padded with zeros for subsequent processing in the average buffer 294.

In the average buffer 294, the frames are averaged together to reduce the uncorrelated noise present. Theoretically, the noise is reduced by a factor of one over the square root of the number of averaged frames, i.e.:

$$\frac{1}{\sqrt{No. Avg Frames}}$$

The frames are averaged in a linear fashion, sample by sample and a new frame is created at the end of the averaging operation. The advantage of this method is that the data is essentially correlated against a slid copy of itself, slid far enough away to avoid averaging the same information content. This provides either a substantial reduction in uncorrelated noise energy for the same amount of sampling time or a substantial reduction in sampling time to obtain the equivalent noise reduction when compared to standard linear averaging.

The minimum limit to the sliding of the data, and to the reuse of old data frame is the autocorrelation function of the data in the frame, which can be predetermined or calculated on-line. This method is equivalent to taking much smaller frames and averaging them together. However, for the purposes of the subsequent Fourier Transformations and filtering taking place, the frame size is required to be large (i.e., 960 samples at 48 kilohertz sampling rate), to obtain several full cycles of each of the tones at $f^1$, $f^2$, and $f^{dp}$. The problem with taking a large number of very small frames is that the Fourier Transforms or other signal processing methods require several cycles of data for proper operation. The method of the present invention outperforms standard linear averaging of large frames because of the reduction in time as well as providing proper operation of the Fourier Transforms.

The final average buffer 296 obtains the averaged data from the average buffer 294, and collects it in a buffer that is used for subsequent processing and signal statistics. The output of the final average buffer 296 is digitally filtered in filter 298 which removes any remaining high or low frequency components not required for final data presentation.

The averaged and filtered data is converted to frequency domain, in the embodiment illustrated, by using a discrete Fourier Transform at block 300, and the resulting data then is ready for presentation to an operator as indicated at block 302. As will be appreciated by those skilled in the art, other signal processing methods are available to convert data, and those other methods are compatible with the device 200.

In further alternate embodiments of the present invention 10, utilized as vibration detectors or alcohol intoximeters, the input/output interface 52 is replaced with, or coupled to, one or more suitable electrical signal sensors configured to measure signals representative of the desired test material, for example, a vibration waveform or an electrical signal representative of breath alcohol content.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

What is claimed is:

1. A sub-microvolt electrical signal testing device, comprising:
    a portable hand-held enclosure;
    a processor housed by said enclosure;
    a memory operatively coupled to said processor, said memory storing one or more operating instructions;
    a display device mounted to said enclosure, said display device being operatively connected to said processor;
    a multi-channel input-output interface operatively coupled to said processor with a bi-directional communications channel, said multi-channel input-output interface configured with at least one input channel to receive external electrical signals and communicate said external electrical signals to said processor;
    a plurality of electrical shock protection components coupled between said at least one input channel and said bi-directional communications channel;
    a switching network coupled between each of said plurality of electrical shock protection components and said bi-directional communications channel, said switching network configured to selectively couple one of a plurality of electrodes to said bi-directional communications channel;
    a differential operational amplifier coupled between said switching network and said bi-directional communications channel, said differential operational amplifier having an adjustable gain setting; and
    wherein said processor is configured to utilize said one or more operating instructions to perform one or more tests on signals received from said multi-channel input-output interface, and to display results of said one or more tests on said display device.

2. The sub-microvolt electrical signal testing device of claim 1 wherein said bi-directional communications channel has a 20-bit signal resolution.

3. The sub-microvolt electrical signal testing device of claim 1 wherein said differential operational amplifier is coupled between said switching network and said bi-directional communications channel by one or more capacitors.

4. The sub-microvolt electrical signal testing device of claim 1 wherein said multi-channel input-output interface includes a common mode cancellation amplifier configured to reduce signal noise levels in said electrical signals.

5. The sub-microvolt electrical signal testing device of claim 1 wherein said multi-channel input-output interface includes an otoacoustic emission testing interface and an auditory brain stem testing interface; and
    wherein said processor is configured with said one or more stored operating instructions for auditory tests selected from the group comprising otoacoustic emission test procedures, auditory brainstem response test procedures, and combinations thereof for a test subject.

6. The sub-microvolt electrical signal testing device of claim 1 further including said processor having an internal memory, said processor configured to utilize said internal memory to execute said one or more operating instructions, whereby signal noise levels from external bus access are reduced.

7. The sub-microvolt electrical signal testing device of claim 1 wherein said multi-channel input-output interface is an otoacoustic emission testing interface, said otoacoustic emission testing interface further comprising:
    at least one output channel;
    at least one transducer operatively connected to said at least one output channel;
    at least one differential operational amplifier coupled between said at least one output channel and said at least one transducer; and
    wherein said at least one transducer is adapted to produce acoustic signals selected from the group comprising pure tones, chirps, clicks, and sine waveforms audible to a human ear.

8. The sub-microvolt electrical signal testing device of claim 7 further comprising:
    at least one microphone operatively connected to said at least one input channel, said microphone configured to receive signals from a human ear and to convert said received signals to electrical signals; and
    at least one dual-stage amplifier coupled between said at least one input channel and said at least one microphone, said dual-stage amplifier configured to provide linear amplification to said electrical signals from said microphone.

9. The sub-microvolt electrical signal testing device of claim 1 wherein said multi-channel input-output interface is housed within said enclosure; and
    wherein said multi-channel input-output interface configured to receive external electrical signals from one or more sensors external to said enclosure which are operatively coupled to said multi-channel input-output interface.

10. The sub-microvolt electrical signal testing device of claim 9 wherein said enclosure includes at least one external connection port, said at least one external connection port operatively coupled to said multi-channel input-output interface for transfer of electrical signals there between.

11. The sub-microvolt electrical signal testing device of claim 1 including at least one digital circuit component and at least one analog circuit component, each of said at least one digital and analog circuit components having a common electrical ground.

12. The sub-microvolt electrical signal testing device of claim 1 wherein said processor is configured for device control of at least said multi-channel input-output interface and for digital signal processing of signals received from said multi-channel input-output interface.

13. The sub-microvolt electrical signal testing device of claim 1 wherein said processor is configured for reduced operations during acquisition of external electrical signals by said multi-channel input-output interface.

14. The sub-microvolt electrical signal testing device of claim 1 wherein said external electrical signals are sub-microvolt electrical signals.

15. The sub-microvolt electrical signal testing device of claim 1 wherein said external electrical signals are amplified sub-microvolt electrical signals.

16. A sub-microvolt electrical signal testing device comprising:

a portable hand-held enclosure;

a processor housed by said enclosure;

a memory operatively coupled to said processor, said memory storing one or more operating instructions;

a display device mounted to said enclosure, said display device being operatively connected to said processor;

a otoacoustic emission testing interface operatively coupled to said processor, said otoacoustic emission testing interface configured to receive external electrical signals and having at least one output channel, at least one transducer operatively connected to said at least one output channel via at least one electrical shock protection component to produce acoustic signals selected from the group comprising pure tones, chirps, clicks, and sine waveforms audible to a human ear, and at least one differential operational amplifier coupled between said at least one output channel and said at least one transducer; and wherein said processor is configured to utilize said one or more operating instructions to perform one or more tests on signals received from said otoacoustic emission testing interface, and to display results of said one or more tests on said display device.

17. A sub-microvolt electrical signal testing device comprising:

a portable hand-held enclosure;

a processor housed by said enclosure;

a memory operatively coupled to said processor, said memory storing one or more operating instructions;

a display device mounted to said enclosure, said display device being operatively connected to said processor;

a otoacoustic emission testing interface operatively coupled to said processor, said otoacoustic emission interface configured with
  (a) at least one input channel and at least one output channel,
  (b) at least one transducer operatively connected to said at least one output channel, said transducer adapted to produce acoustic signals selected from the group comprising pure tones, chirps, clicks, and sine waveforms audible to a human ear,
  (c) at least one differential operational amplifier coupled between said at least one output channel and said at least one transducer,
  (d) at least one microphone operatively connected to said at least one input channel to receive signals from a human ear,
  (e) at least one electrical shock protection component coupled between said at least one input channel and said at least one microphone,
  (d) at least one dual-stage amplifier coupled between said at least one input channel and said at least one microphone, said dual-stage amplifier configured to provide linear amplification to said received signals; and wherein said processor is configured to utilize said operating instructions to perform at least one test on signals received from said otoacoustic emission interface, and to display results of said test on said display device.

18. A sub-microvolt electrical signal testing device comprising:

a portable hand-held enclosure;

a processor housed by said enclosure;

a memory operatively coupled to said processor, said memory storing one or more operating instructions;

a display device mounted to said enclosure, said display device being operatively connected to said processor;

an auditory brain stem testing interface having
  (a) a plurality of electrodes, each of said electrodes adapted to receive external electrical signals;
  (b) a bi-directional communications channel operatively connected to said plurality of electrodes;
  (c) a plurality of electrical shock protection components coupled between each of said plurality of electrodes and said bi-directional communications channel;
  (d) a switching network coupled between each of said plurality of electrical shock protection components and said bi-directional communications channel, said switching network configured to selectively couple one of said plurality of electrodes to said bi-directional communications channel; and
  (e) a differential operational amplifier coupled between said switching network and said bi-directional communications channel, said differential operational amplifier having an adjustable gain setting; and wherein said processor is configured to utilize said one or more operating instructions to perform one or more tests on signals received from said auditory brain stem testing interface, and to display results of said one or more tests on said display device.

19. The sub-microvolt electrical signal testing device of claim 18 wherein said plurality of electrical shock protection components includes at least one surge suppression component.

20. The sub-microvolt electrical signal testing device of claim 18 further comprising a common mode cancellation amplifier coupled between said switching network and said differential operational amplifier, said common mode cancellation amplifier configured to reduce signal noise levels between said plurality of electrodes and said bi-directional communications channel.

21. The sub-microvolt electrical signal testing device of claim 18 wherein said differential operational amplifier is configured with a first gain setting to amplify a signal from one of said plurality of electrodes, and said differential operational amplifier is configured with a second gain setting to facilitate impedance testing of said plurality of electrodes.

22. The sub-microvolt electrical signal testing device of claim 21 wherein said switching network is further configured to select between said first gain setting and said second gain setting on said differential operational amplifier.

* * * * *